United States Patent [19]

Höök et al.

[11] Patent Number: 5,175,096
[45] Date of Patent: Dec. 29, 1992

[54] DNA ENCODING A FIBRONECTIN BINDING PROTEIN AS WELL AS ITS PREPARATION

[75] Inventors: Magnus Höök, Birmingham, Ala.; Klas Jönsson, Studentvägen, Sweden; Kjell M. Lindberg, Kornvägen, Sweden; Christer Signäs, Hamnesplanaden, Sweden

[73] Assignee: Alfa-Laval Agri International Aktiebolag, Tumba, Sweden

[21] Appl. No.: 520,808

[22] Filed: May 9, 1990

[30] Foreign Application Priority Data

May 11, 1989 [SE] Sweden .................................. 8901687

[51] Int. Cl.$^5$ ...................... C07K 13/00; C12N 15/31; C12N 15/63
[52] U.S. Cl. .............................. 435/69.1; 435/172.3; 435/252.3; 435/320.1; 530/350; 536/27
[58] Field of Search ................. 435/69.1, 172.3, 320.1, 435/252.3; 536/27; 530/350

[56] References Cited

PUBLICATIONS

Embo, J., vol. 6: 2351 to 2357, Aug. 1987, Flock et al. Cloning and Expression of the Gene for a Fibronectin-binding protein from Staphylococcus Aureus.

Infect and Immun. vol. 37:526 to 531, Aug. 1982, Espersen et al., Isolation of a Fibronectin-Binding Protein from Staphylococcus Aureus.

P.N.A.S. vol. 80:697 to 701, Feb. 1983, Löfdahl et al. Gene for Staphyloccal Protein A.

*Primary Examiner*—David L. Lacey
*Assistant Examiner*—John D. Ulm
*Attorney, Agent, or Firm*—Burns, Doane, Swecker & Mathis

[57] ABSTRACT

The present invention relates to a new recombinant hybrid-DNA-molecule comprising a nucleotide sequence from *S. aureus* coding for a protein, or polypeptide, having fibronectin binding properties.

6 Claims, 8 Drawing Sheets

```
  1 GTTAACAACA ATCTTAACTT TTTATTAACT CGCTTTTTTT CATTGCTTTT
 51 AAAAACCGAA CAATATAGAA TTGCATTTAT TGAGTTTTTA AATAAATGA
101 ATTTGCATT TAAGGAGAA TATTATAGTG AAAAGCAATC TTAGATACGG
151 CATAAGAAAA CACAAATTGG GAGCGGCCTC AGTATTCTTA GGAACAATGA
201 TCGTTGTTGG AATGGGACAA GAAAAAGAAG CTGCAGCATC GGAACAAAAC
251 AATACTACAG TAGAGGAAAG TGGGAGTTCA GCTACTGAAA GTAAAGCAAG
301 CGAAACACAA ACAACTACAA ATAACGTTAA TACAATAGAT GAAACACAAT
351 CATACAGCGC GACATCAACT GAGCAACCAT CACAATCAAC ACAAGTAACA
401 ACAGAAGAAG CACCGAAAAC TGTGCAAGCA CCAAAAGTAG AAACTTCGCG
451 AGTTGATTTG CCATCGGAAA AAGTTGCTGA TAAGGAAACT ACAGGAACTC
501 AAGTTGACAT AGCTCAACAA AGTAAAGTCT CAGAAATTAA ACCAAGAATG
551 AAAAGATCAA CTGACGTTAC AGCAGTTGCA GAGAAAGAAG TAGTGGAAGA
601 AACTAAAGCG ACAGGTACAG ATGTAACAAA TAAAGTGGAA GTAGAGAAG
651 GTAGTGAAAT TGTAGGACAT AAACAAGATA CGAATGTTGT AAATCCTCAT
701 AACGCAGAAA GAGTAACCTT GAAATATAAA TGGAAATTTG GAGAAGGAAT
751 TAAGGCGGGA GATTATTTTG ATTTCACATT AAGCGATAAT GTTGAAACTC
801 ATGGTATCTC AACACTGCGT AAAGTTCCGG AGATAAAAAG TACAGATGGT
851 CAAGTTATGG CGACAGGAGA AATAATTGGA GAAAGAAAAG TTAGATATAC
901 GTTTAAAGAA TATGTACAAG AAAAGAAAGA TTTAACTGCT GAATTATCTT
951 TAAATCTATT TATTGATCCT ACAACAGTGA CGCAAAAAGG TAACCAAAAT
```

```
1001 GTTGAAGTTA AATTGGGTGA GACTACGGTT AGCAAAATAT TTAATATTCA
1051 ATATTTAGGT GGAGTTAGAG ATAATTGGGG AGTAACAGCT AATGGTCGAA
1101 TTGATACTTT AAATAAAGTA GATGGGAAAT TTAGTCATTT TGCCGTACATG
1151 AAACCTAACA ACCAGTCGTT AAGCTCTGTG ACAGTAACTG GTCAAGTAAC
1201 TAAAGGAAAT AAACCAGGGG TTAATAATCC AACAGTTAAG GTATATAAAC
1251 ACATTGGTTC AGACGATTTA GCTGAAAGCG TATATGCAAA GCTTGATGAT
1301 GTCAGCAAAT TTGAAGATGT GACTGATAAT ATGAGTTTAG ATTTGATAC
1351 TAATGGTGGT TATTCTTTAA ACTTTAATAA TTTAGACCAA AGTAAAAATT
1401 ATGTAATAAA ATATGAAGGG TATTATGATT CAAATGCTAG CAACTTAGAA
1451 TTTCAAACAC ACCTTTTTGG ATATTATAAC TATTATTATA CAAGTAATTT
1501 AACTTGGAAA AATGGCGTTG CATTTTACTC TAATAACGCT CAAGGCGACG
1551 GCAAAGATAA ACTAAAGGAA CCTATTATAG AACATAGTAC TCCTATCGAA
1601 CTTGAATTTA AATCAGAGCC GCCAGTGGAG AAGCATGAAT TGACTGGTAC
1651 AATCTGTTGAA AGTAATGATT CTAAGCCAAT TGATTTTGAA TATCATACAG
1701 CTGTTGAAGG TGCAGAAGGT CATGCAGAAG GTACCATTGA AACTGAAGAA
1751 GATTCTATTC ATGTAGACTT TGAAGAATCG ACACATGAAA ATTCAAAACA
1801 TCATGCTGAT GTTGTTGAAT ATGAAGAAGA TACAAACCCA GGTGGTGGTC
1851 AGGTTACTAC TGAGTCTAAC CTAGTTGAAT TTGACGAAGA TTCTACAAAA
1901 GGTATTGTAA CTGGTGCTGT TAGCGATCAT ACAACAATTG AAGATACGAA
1951 AGAATATACG ACTGAAAGTA ACTTGATTGA ACTAGTAGAT GAACTACCTG
```

FIG.1:3

```
2001  AAGAACATGG  TCAAGCGCAA  GGACCAATCG  AGGAAATTAC  TGAAAACAAT
2051  CATCATATTT  CTCATTCTGG  TTTAGGAACT  GAAAATGGTC  ACGGTAATTA
2101  TGGCGTGATT  GAAGAAATCG  AAGAAAATAG  CCACGTGGAT  ATTAAGAGTG
2151  AATTAGGTTA  CGAAGGTGGC  CAAATAGCG   GTAATCAGTC  ATTTGAGGAA
2201  GACACAGAAG  AAGATAAACC  GAAATATGAA  CAAGGTGGCA  ATATCGTAGA
2251  TATCGATTTC  GATAGTGTAC  CTCAAATTCA  TGGTCAAAAT  AATGGTAACC
2301  AATCATTCGA  AGAAGATACA  GAGAAAGACA  AACCTAAGTA  TGAACAAGGT
2351  GGTAATATCA  TTGATATCGA  CTTCGACAGT  GTGCCACATA  TTCACGGATT
2401  CAATAAGCAC  ACTGAAATTA  TTGAAGAAGA  TACAAATAAA  GATAAACCAA
2451  ATTATCAATT  CGGTGGACAC  AATAGTGTTG  ACTTTGAAGA  AGATACACTT
2501  CCACAAGTAA  GTGGTCATAA  TGAAGGTCAA  CAAACGATTG  AAGAAGATAC
2551  AACACCTCCA  ATCGTGCCAC  CAACGCCACC  GACACCAGAA  GTACCAAGCG
2601  AGCCGGAAAC  ACCAACACCA  CCGACACCAG  AAGTACCAAG  CGAGCCGGAA
2651  ACACCAACAC  CGCCAACGCC  AGAGGTACCA  ACTGAACCTG  GTAAACCAAT
2701  ACCACCTGCT  AAAGAAGAAC  CTAAAAAACC  TTCTAAACCA  GTGGAACAAG
2751  GTAAAGTAGT  AACACCTGTT  ATTGAAATCA  ATGAAAAGGT  TAAAGCAGTG
2801  GTACCAACTA  AAAAAGCACA  ATCTAAGAAA  TCTGAACTAC  CTGAAACAGG
2851  TGGAGAAGAA  TCAACAAACA  ACGGCATGTT  GTTCGGCGGA  TTATTTAGCA
2901  TTTTAGGTTT  AGCGTTATTA  CGCAGAAATA  AAAAGAATCA  CAAAGCATAA
2951  TCAATCCAAA  ATTGACAGGT  TTATTTCATA  AATTATATGA  AGTAAGCCTG
```

```
3001  TTTTTAAAA  TTAAAACAAA  TTTCCCAAGA  AATAATTACA  TACTCAATGA
3051  CACTATGAAG  GCGTTCTAAT  TAGTGTTAAA  ATGACGTTGA  TACATAGATT
3101  TAATACTTAG  GAAAAGGAGC  ACATTAACTT  TGAAAAAAAT  AAAAAAGGCA
3151  ATCATTCCCG  CTGCTGGTTT  AGGGACTAGA  TTTTTACCAG  CAACTAAAGC
3201  GATGCCAAAG  GAAATGCTTC  CTATCTTAGA  TAAACCCACA  ATACAATATA
3251  TCGTTGAAGA  AGCTGCAAGA  GCTGGAATTG  AAGATATTAT  TATAGTGACA
3301  GGTCGCCACA  AACGCGCGAT  TGAAGATCAT  TTTGATAGTC  AAAAGAATT
3351  AGAAATGGTG  TTAAAAGAAA  AAGGTAAATC  TGAATTACTA  GAGAAAGTTC
3401  AGTATTCAAC  GGAACTTGCG  AATATTTTT  ATGTAAGGCA  GAAAGAACAA
3451  AAAGGTTTAG  GGCATGC
```

FIG. 1:4

```
LGTENGHGNYDVIEEIEENSHVDIKSELGYEGGQNSGNQSFEEDTEEDKPKYEQGGNIVD        772
||||||||||||| || ||||||||||||||||||||||||||||||||||||||||||
LGTENGHGNYGVIEEIEENSHVDIKSELGYEGGQNSGNQSFEEDTEEDKPKYEQGGNIVD        708

IDFDSVPQIHGQNKGNQSFEEDTEKDKPKYEHGGNIIDIDFDSVPHIHGFNKHTEIIEED        832
||||||||||| |||||||||||||||||| |||||||||||||||||||||||||||
IDFDSVPQIHGQNNGNQSFEEDTEKDKPKYEQGGNIIDIDFDSVPHIHGFNKHTEIIEED       768

TNKDKPSYQFGGHNSVDFEEDTLPKVSGQNEGQQTIEEDTTPPIVPPTPPTPEVPSEPET        892
|||||| ||||||||||||||||  ||||||||||||||||| ||
TNKDKPNYQFGGHNSVDFEEDTLPQVSGHNEGQQTIEEDTTPPIVP............         814

PTPPTPEVPSEPETPTPPTPEVPSEPETPTPPTPEVPAEPGKPVPPAKEEPKKPSKPVEQ        952
|||||||||||||||||||||||||||||| ||||| ||||| ||||||||||||||||
PTPPTPEVPSEPETPTPPTPEVPSEPETPTPPTPEVPTEPGKPIPPAKEEPKKPSKPVEQ       874

GKVVTPVIEINEKVKAVAPTKKPQSKKSELPETGGEESTNKGMLFGGLFSILGLALLRRN      1012
||||||||||||||||| |||| |||||||||||||| ||||||||| ||||||||||
GKVVTPVIEINEKVKAVVPTKKAQSKKSELPETGGEESTNNGMLFGGLFSILGLALLRRN      934

KKNHKA                                                            1018
||||||
KKNHKA                                                             940
```

```
  1  VKSNLRYGIR  KHKLGAASVF  LGTMIVVGMG  QEKEAAASEQ  NNTTVEESGS
 51  SATESKASET  QTTTNNVNTI  DETQSYSATS  TEQPSQSTQV  TTEEAPKTVQ
101  APKVETSRVD  LPSEKVADKE  TTGTQVDIAQ  QSKVSEIKPR  MKRSTDVTAV
151  AEKEVVEETK  ATGTDVTNKV  EVEEGSEIVG  HKQDTNVVNP  HNAERVTLKY
201  KWKFGEGIKA  GDYFDFTLSD  NVETHGISTL  RKVPEIKSTD  GQVMATGEII
251  GERKVRYTFK  EYVQEKKDLT  AELSLNLFID  PTTVTQKGNQ  NVEVKLGETT
301  VSKIFNIQYL  GGVRDNWGVT  ANGRIDTLNK  VDGKFSHFAY  MKPNNQSLSS
351  VTVTGQVTKG  NKPGVNNPTV  KVYKHIGSDD  LAESVYAKLD  DVSKFEDVTD
401  NMSLDFDTNG  GYSLNFNNLD  QSKNYVIKYE  GYDSNASNL   EFQTHLFGYY
451  NYYTSNLTW   KNGVAFYSNN  AQGDGKDKLK  EPIIEHSTPI  ELEFKSEPPV
501  EKHELTGTIE  ESNDSKPIDF  EYHTAVEGAE  GHAEGTIETE  EDSIHVDFEE
551  STHENSKHHA  DVVEYEEDTN  PGGGQVTTES  NLVEFDEDST  KGIVTGAVSD
601  HTTIEDTKEY  TTESNLIELV  DELPEEHGQA  QGPIEEITEN  NHHISHSGLG
651  TENGHGNYGV  IEEIEENSHV  DIKSELGYEG  GQNSGNQSFE  EDTEEDKPKY
701  EQGGNIVDID  FDSVPQIHGQ  NNGNQSFEED  TEKDKPKYEQ  GGNIIDIDFD
751  SVPHIHGFNK  HTEIIEEDTN  KDKPNYQFGG  HNSVDFEEDT  LPQVSGHNEG
801  QQTIEEDTTP  PIVPPTPPTP  EVPSEPETPT  PPTPEVPSEP  ETPTPPTPEV
851  PTEPGKPIPP  AKEEPKKPSK  PVEQGKVVTP  VIEINEKVKA  VVPTKKAQSK
901  KSELPETGGE  ESTNNGMLFG  GLFSILGLAL  LRRNKKNHKA
```

DNA ENCODING A FIBRONECTIN BINDING PROTEIN AS WELL AS ITS PREPARATION

TECHNICAL FIELD

The present invention relates to a fibronectin binding protein as well as hybrid-DNA-molecules, e.g. plasmids or phages comprising a nucleotide sequence coding for said protein. Further the invention relates to microorganisms comprising said molecules and their use producing said protein, as well as the synthetic preparation of said protein.

The object of the present invention is to obtain a minimal fibronectin binding protein.

A further object is to obtain said protein by means of a genetic engineering technique by using e.g. a plasmid comprising a nucleotide sequence coding for said protein.

A further object is to obtain a possibility of preparing said protein by chemical synthesis.

Further objects will be apparent from the following description.

BACKGROUND OF THE INVENTION

WO-A1-85/05553 discloses bacterial cell surface proteins having fibronectin, fibrinogen, collagen, and/or laminin binding ability. Thereby it is shown that different bacteria have an ability to bind to fibronectin, fibrinogen, collagen, and/or laminin. It is further shown that fibronectin binding protein has a molecular weight of 165 kD and/or 87 kD, whereby it is probable that the smaller protein is a part of the larger one.

Fibronectin is a large glycoprotein ($M_r$ ca 450 kd) with two similar subunits, which may vary in molecular size depending on a complex splicing pattern of a precursor mRNA (1). The major function of fibronectin, which is found in body fluids, blood clots and extracellular matrices, seems to be related to the ability of the protein to mediate substrate adhesion of most eukaryotic cells (2, 3, 4, 5.)

In the late seventies, Kuusela found that fibronectin not only interacts with eucaryotic cells but also binds to cells of *Staphylococcus aureus* (6). Since this observation, a number of pathogenic microorganisms have been shown to bind to fibronectin with a high degree of specificity and a high affinity, such as streptococci (group A, C, and G), coagulase negative staphylococci, *E. coli* and *Treponema pallidum*. Fibronectin in the extracellular matrix appears to serve as a substratum also for the adhesion of different microorganisms. The binding of fibronectin may for some microorganisms represent a crucial step in the colonization of host tissue and development of infection.

Several different cell surface components have been implicated as fibronectin receptors on Gram-positive bacteria including lipotechioc acid (8, 9) and protein (10). In previous studies a fibronectin binding protein with a $M_r$ of 197-210 kD has been isolated from *S. aureus* strain Newman (11, 12) and tentatively identified as a fibronectin receptor. The binding site in fibronectin for eukaryotic cells has been localized to a tetrapeptide (ArgGlyAspSer) in the central portion of each of the two subunits forming the fibronectin, which is different to the binding site of most bacteria so far studied. The bacteria appear to bind to the aminoterminal 29 kDa domain of the fibronectin subunit.

An eukaryotic receptor has been identified as a 140 kDa complex in the cell membrane, whereas the bacterial fibronectin binding protein (FNBP) of *Staphylococcus aureus* strain Newman has been identified as a 210 kDa protein. From previous studies (SE-A-8702272-9) it has been reported of the cloning, expression and the complete nucleotide sequence of a gene (herein called gene 1) for a FNBP in *Staphylococcus aureus*.

In the present application the cloning, expression and the nucleotide sequence of a further gene, gene 2, located downstream the previous studied and reported fibronectin binding protein sequence. To further characterize this fibronectin binding protein from *S aureus*, the gene for this protein has been cloned in *E. coli*. The fibronectin binding domain within this protein has also been localized.

BRIEF DESCRIPTION OF THE DRAWINGS

FIGS. 1:1 to 1:3 depicts the nucleotide sequence of the nucleic acid encoding the fibronectin binding protein.

FIG. 2 presents a comparison between the amino acid sequences of the fibronectin binding proteins encoded by gene 1 and gene 2, respectively, which are given in parallel.

FIG. 4 is the deduced amino acid sequence of the cloned fnbB from *S. aureus* strain 8325-4.

DESCRIPTION OF THE INVENTION

Figure 3:
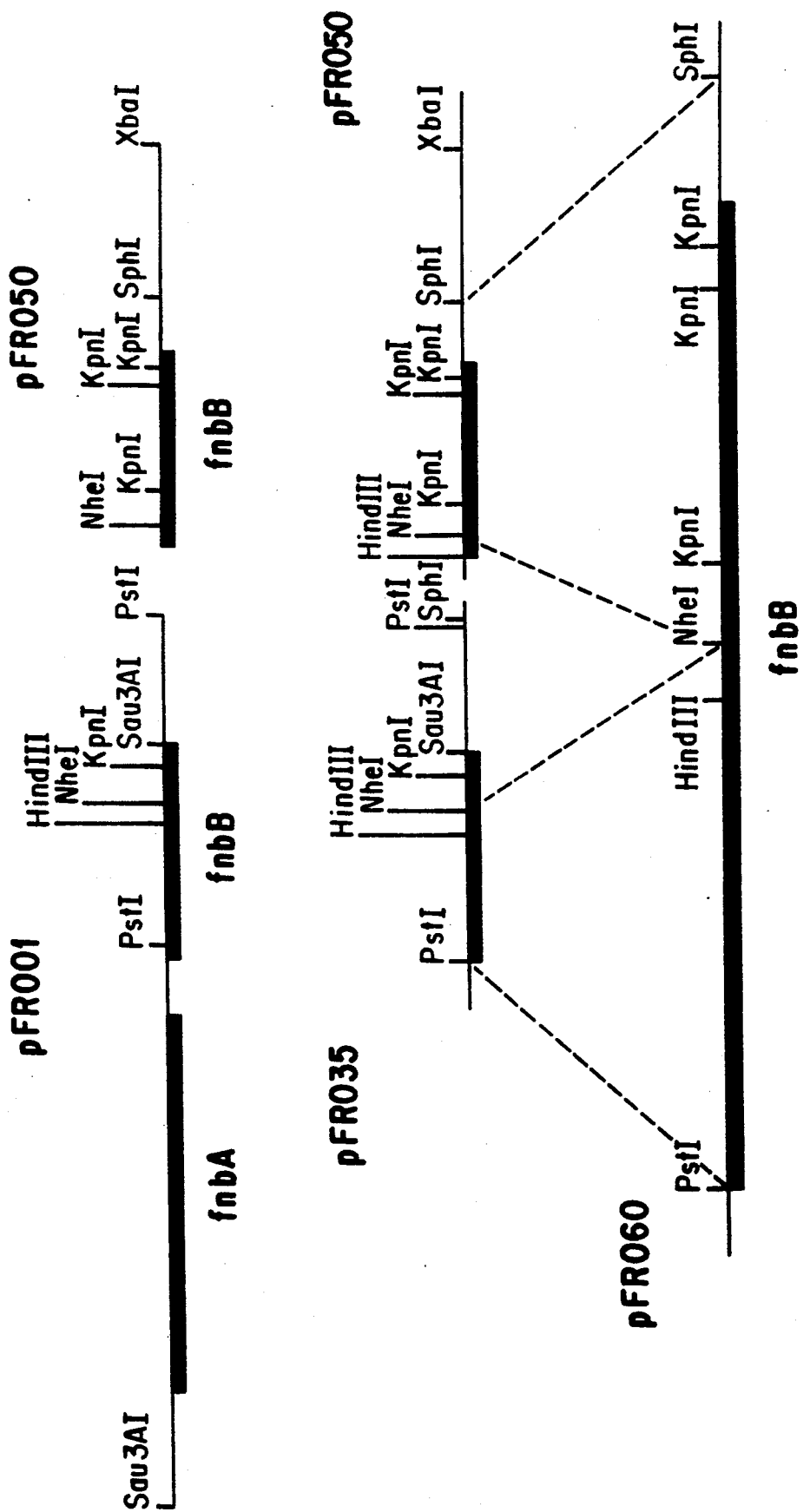
FIG. 3 is a restriction map of the original clones pFR0001 and pFR050 together with subclones pFR035 and pFR036. The location of fnbA and fnbB is indicated. The sequenced fragment of the insert is shown in more detail. The coding sequence in each clone are shown with bold lines.
Figure 5:
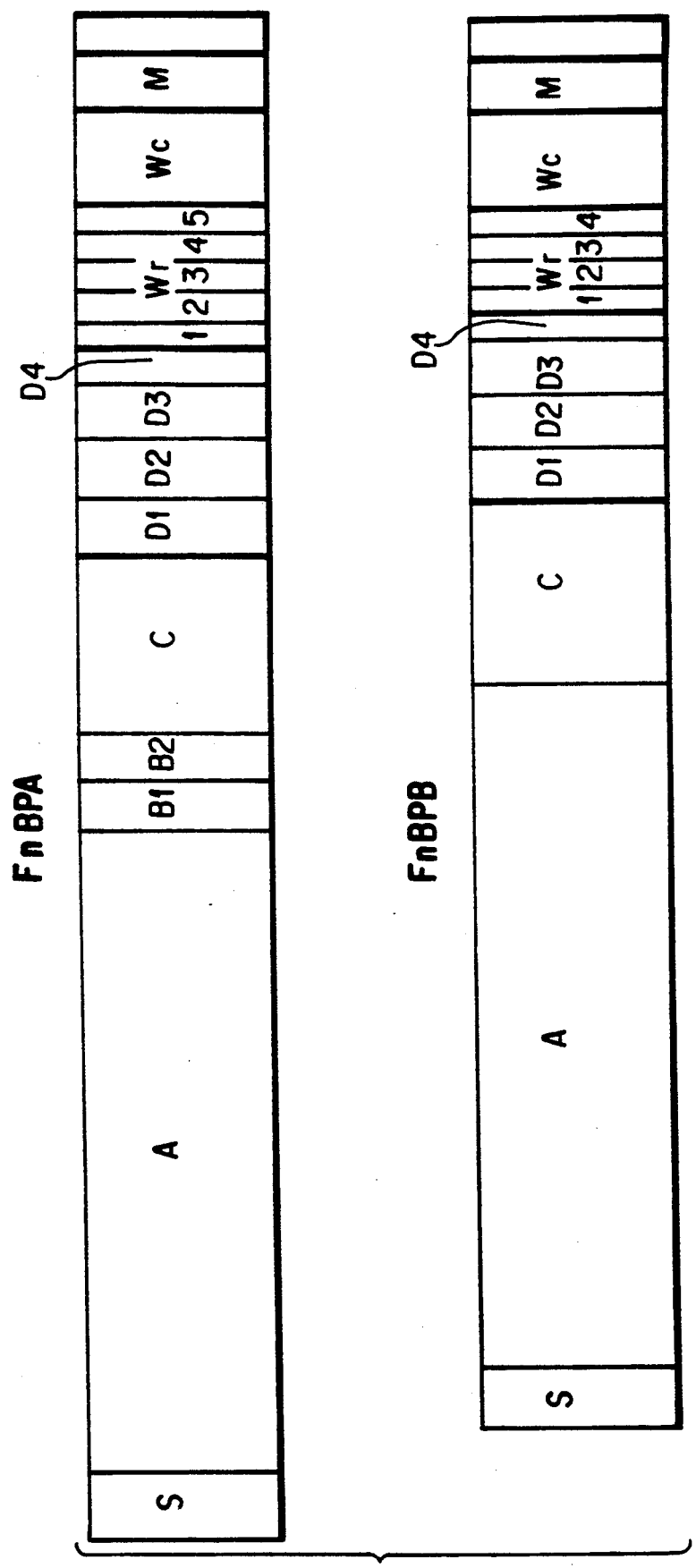
FIG. 5 is a schematic drawing comparing domain organization of FnBPA and FnBPB.

It has now surprisingly been found possible to obtain a hybride-DNA-molecule comprising a nucleotide sequence coding for a protein or a polypeptide having fibronectin binding properties. As evident from below the following nucleotide sequence is present in the gene coding for said protein:

| | | | | |
|---|---|---|---|---|
| GTTAACAACA | ATCTTAACTT | TTTATTAACT | CGCTTTTTTT | CATTGCTTTT |
| AAAAACCGAA | CAATATAGAA | TTGCATTTAT | TGAGTTTTTA | AAATAAATGA |
| ATTTTGCATT | TAAGGGAGAA | TATTATAGTG | AAAAGCAATC | TTAGATACGG |
| CATAAGAAAA | CACAAATTGG | GAGCGGCCTC | AGTATTCTTA | GGAACAATGA |
| TCGTTGTTGG | AATGGGACAA | GAAAAAGAAG | CTGCAGCATC | GGAACAAAAC |
| AATACTACAG | TAGAGGAAAG | TGGGAGTTCA | GCTACTGAAA | GTAAAGCAAG |
| CGAAACACAA | ACAACTACAA | ATAACGTTAA | TACAATAGAT | GAAACACAAT |
| CATACAGCGC | GACATCAACT | GAGCAACCAT | CACAATCAAC | ACAAGTAACA |
| ACAGAAGAAG | CACCGAAAAC | TGTGCAAGCA | CCAAAAGTAG | AAACTTCGCG |
| AGTTGATTTG | CCATCGGAAA | AAGTTGCTGA | TAAGGAAACT | ACAGGAACTC |
| AAGTTGACAT | AGCTCAACAA | AGTAAAGTCT | CAGAAATTAA | ACCAAGAATG |
| AAAAGATCAA | CTGACGTTAC | AGCAGTTGCA | GAGAAAGAAG | TAGTGGAAGA |
| AACTAAAGCG | ACAGGTACAG | ATGTAACAAA | TAAAGTGGAA | GTAGAAGAAG |
| GTAGTGAAAT | TGTAGGACAT | AAACAAGATA | CGAATGTTGT | AAATCCTCAT |

-continued

| | | | | |
|---|---|---|---|---|
| AACGCAGAAA | GAGTAACCTT | GAAATATAAA | TGGAAATTTG | GAGAAGGAAT |
| TAAGGCGGGA | GATTATTTTG | ATTTCACATT | AAGCGATAAT | GTTGAAACTC |
| ATGGTATCTC | AACACTGCGT | AAAGTTCCGG | AGATAAAAAG | TACAGATGGT |
| CAAGTTATGG | CGACAGGAGA | AATAATTGGA | GAAAGAAAAG | TTAGATATAC |
| GTTTAAAGAA | TATGTACAAG | AAAAGAAAGA | TTTAACTGCT | GAATTATCTT |
| TAAATCTATT | TATTGATCCT | ACAACAGTGA | CGCAAAAAGG | TAACCAAAAT |
| GTTGAAGTTA | AATTGGGTGA | GACTACGGTT | AGCAAAATAT | TTAATATTCA |
| ATATTTAGGT | GGAGTTAGAG | ATAATTGGGG | AGTAACAGCT | AATGGTCGAA |
| TTGATACTTT | AAATAAAGTA | GATGGGAAAT | TTAGTCATTT | TGCGTACATG |
| AAACCTAACA | ACCAGTCGTT | AAGCTCTGTG | ACAGTAACTG | GTCAAGTAAC |
| TAAAGGAAAT | AAACCAGGGG | TTAATAATCC | AACAGTTAAG | GTATATAAAC |
| ACATTGGTTC | AGACGATTTA | GCTGAAAGCG | TATATGCAAA | GCTTGATGAT |
| GTCAGCAAAT | TTGAAGATGT | GACTGATAAT | ATGAGTTTAG | ATTTTGATAC |
| TAATGGTGGT | TATTCTTTAA | ACTTTAATAA | TTTAGACCAA | AGTAAAAATT |
| ATGTAATAAA | ATATGAAGGG | TATTATGATT | CAAATGCTAG | CAACTTAGAA |
| TTTCAAACAC | ACCTTTTTGG | ATATTATAAC | TATTATTATA | CAAGTAATTT |
| AACTTGGAAA | AATGGCGTTG | CATTTTACTC | TAATAACGCT | CAAGGCGACG |
| GCAAAGATAA | ACTAAAGGAA | CCTATTATAG | AACATAGTAC | TCCTATCGAA |
| CTTGAATTTA | AATCAGAGCC | GCCAGTGGAG | AAGCATGAAT | TGACTGGTAC |
| AATCGAAGAA | AGTAATGATT | CTAAGCCAAT | TGATTTTGAA | TATCATACAG |
| CTGTTGAAGG | TGCAGAAGGT | CATGCAGAAG | GTACCATTGA | AACTGAAGAA |
| GATTCTATTC | ATGTAGACTT | TGAAGAATCG | ACACATGAAA | ATTCAAAACA |
| TCATGCTGAT | GTTGTTGAAT | ATGAAGAAGA | TACAAACCCA | GGTGGTGGTC |
| AGGTTACTAC | TGAGTCTAAC | CTAGTTGAAT | TTGACGAAGA | TTCTACAAAA |
| GGTATTGTAA | CTGGTGCTGT | TAGCGATCAT | ACAACAATTG | AAGATACGAA |
| AGAATATACG | ACTGAAAGTA | ACTTGATTGA | ACTAGTAGAT | GAACTACCTG |
| AAGAACATGG | TCAAGCGCAA | GGACCAATCG | AGGAAATTAC | TGAAAACAAT |
| CATCATATTT | CTCATTCTGG | TTTAGGAACT | GAAATGGTC | ACGGTAATTA |
| TGGCGTGATT | GAAGAAATCG | AAGAAAATAG | CCACGTGGAT | ATTAAGAGTG |
| AATTAGGTTA | CGAAGGTGGC | CAAAATAGCG | GTAATCAGTC | ATTTGAGGAA |
| GACACAGAAG | AAGATAAACC | GAAATATGAA | CAAGGTGGCA | ATATCGTAGA |
| TATCGATTTC | GATAGTGTAC | CTCAAATTCA | TGGTCAAAAT | AATGGTAACC |
| AATCATTCGA | AGAAGATACA | GAGAAAGACA | AACCTAAGTA | TGAACAAGGT |
| GGTAATATCA | TTGATATCGA | CTTCGACAGT | GTGCCACATA | TTCACGGATT |
| CAATAAGCAC | ACTGAAATTA | TTGAAGAAGA | TACAAATAAA | GATAAACCAA |
| ATTATCAATT | CGGTGGACAC | AATAGTGTTG | ACTTTGAAGA | AGATACACTT |
| CCACAAGTAA | GTGGTCATAA | TGAAGGTCAA | CAAACGATTG | AAGAAGATAC |
| AACACCTCCA | ATCGTGCCAC | CAACGCCACC | GACACCAGAA | GTACCAAGCG |
| AGCCGGAAAC | ACCAACACCA | CCGACACCAG | AAGTACCAAG | CGAGCCGGAA |
| ACACCAACAC | CGCCAACGCC | AGAGGTACCA | ACTGAACCTG | GTAAACCAAT |
| ACCACCTGCT | AAAGAAGAAC | CTAAAAAACC | TTCTAAACCA | GTGGAACAAG |
| GTAAAGTAGT | AACACCTGTT | ATTGAAATCA | ATGAAAAGGT | TAAAGCAGTG |
| GTACCAACTA | AAAAAGCACA | ATCTAAGAAA | TCTGAACTAC | CTGAAACAGG |
| TGGAGAAGAA | TCAACAAACA | ACGGCATGTT | GTTCGGCGGA | TTATTTAGCA |
| TTTTAGGTTT | AGCGTTATTA | CGCAGAAATA | AAAAGAATCA | CAAAGCATAA |
| TCAATCCAAA | ATTGACAGGT | TTATTTCATA | AATTATATGA | AGTAAGCCTG |
| TTTTTTAAAA | TTAAAACAAA | TTTCCCAAGA | AATAATTACA | TACTCAATGA |
| CACTATGAAG | GCGTTCTAAT | TAGTGTTAAA | ATGACGTTGA | TACATAGATT |
| TAATACTTAG | GAAAAGGAGC | ACATTAACTT | TGAAAAAAAT | AAAAAAGGCA |
| ATCATTCCCG | CTGCTGGTTT | AGGGACTAAG | TTTTTACCAG | CAACTAAAGC |
| GATGCCAAAG | GAAATGCTTC | CTATCTTAGA | TAAACCCACA | ATACAATATA |
| TCGTTGAAGA | AGCTGCAAGA | GCTGGAATTG | AAGATATTAT | TATAGTGACA |
| GGTCGCCACA | AACGCGCGAT | TGAAGATCAT | TTTGATAGTC | AAAAAGAATT |
| AGAAATGGTG | TTAAAAGAAA | AAGGTAAATC | TGAATTACTA | GAGAAGTTC |
| AGTATTCAAC | GGAACTTGCG | AATATTTTTT | ATGTAAGGCA | GAAAGAACAA |
| AAAGGTTTAG | GGCATGC | | | | whereby this nucleotide sequence encodes for the following protein starting at nucleotide no. 128 in the reading above, whereby the prepresent nucleotides are part of the signal system:

| | | | | |
|---|---|---|---|---|
| VKSNLRYGIR | KHKLGAASVF | LGTMIVVGMG | QEKEAAASEQ | NNTTVEESGS |
| SATESKASET | QTTTNNVNTI | DETQSYSATS | TEQPSQSTQV | TTEEAPKTVO |
| APKVETSRVD | LPSEKVADKE | TTGTQVDIAQ | QSKVSEIKPR | MKRSTDVTAV |
| AEKEVVEETK | ATGTDVTNKV | EVEEGSEIVG | HKQDTNVVNP | HNAERVTLKY |
| KWKFGEGIKA | GDYFDFTLSD | NVETHGISTL | RKVPEIKSTD | GQVMATGEII |
| GERKVRYTFK | EYVQEKKDLT | AELSLNLFID | PTTVTQKGNQ | NVEVKLGETT |
| VSKIFNIQYL | GGVRDNWGVT | ANGRIDTLNK | VDGKFSHFAY | MKPNNQSLSS |
| VTVTGQVTKG | NKPGVNNPTV | KVYKHIGSDD | LAESVYAKLD | DVSKFEDVTD |
| NMSLDFDTNG | GYSLNFNNLD | QSKNYVIKYE | GYYDSNASNL | EFQTHLFGYY |
| NYYYTSNLTW | KNGVAFYSNN | AQGDGKDKLK | EPIIEHSTPI | ELEFKSEPPV |
| EKHELTGTIE | ESNDSKPIDF | EYHTAVEGAE | GHAEGTIETE | EDSIHVDFEE |
| STHENSKHHA | DVVEYEEDTN | PGGGQVTTES | NLVEFDEDST | KGIVTGAVSD |
| HTTIEDTKEY | TTESNLIELV | DELPEEHGQA | QGPIEEITEN | NHHISHSGLG |
| TENGHGNYGV | IEEIEENSHV | DIKSELGYEG | GQNSGNQSFE | EDTEEDKPKY |
| EQGGNIVDID | FDSVPQIHGQ | NNGNQSFEED | TEKDKPKYEQ | GGNIIDIDFD |
| SVPHIHGFNK | HTEIIEEDTN | KDKPNYQFGG | HNSVDFEEDT | LPQVSGHNEG |
| QQTIEEDTTP | PIVPPTPPTP | EVPSEPETPT | PPTPEVPSEP | ETPTPPTPEV |

-continued

| | | | | |
|---|---|---|---|---|
| PTEPGKPIPP | AKEEPKKPSK | PVEQGKVVTP | VIEINEKVKA | VVPTKKAQSK |
| KSELPETGGE | ESTNNGMLFG | GLFSILGLAL | LRRNKKNHKA | |

In the single letter amino acid sequence above the following abbreviations have been used A Ala, Alanine
R Arg, Arginine
N Asn, Asparagine
D Asp, Aspartic acid
C Cys, Cysteine
C Cys, Cysteine
G Gly, Clycine
E Glu, Glutamic acid
Q Gln, Glutamine
H His, Histidine
I Ile, Isoleucine
L Leu, Leucine
K Lys, Lysine
M Met, Methionine
F Phe, Phenylalanine
P Pro, Proline
S Ser, Serine
T Thr, Threonine
W Trp, Tryptophan
Y Tyr, Tyrosine
V Val, Valine Above, the nucleotide sequence of the starting signal ends at nucleotide 235 and the sequence starting at nucleotide no. 1735 shows the nucleotide sequence of the binding region, which corresponds to the following amino acid sequence

| | | | | | |
|---|---|---|---|---|---|
| IETEEDSIHV | DFEESTHHEN | SKHHADVVEY | EEDTNPGGGQ | VTTESNLVEF | |
| DEDSTKGIVT | GAVSDHTTIE | DTKEYTTESN | LIELVDELPE | EHGQAQGPIE | |
| EITENNHHIS | HSGLGTENGH | GNYGVIEEIE | ENSHVDIKSE | LGYEGGQNSG | |
| NQSFEEDTEE | DKPKYEQGGG | NIVDIDFDSV | PQIHGQNNGN | QSFEEDTEKD | |
| KPKYEQGGNI | IDIDFDSVPH | IHGFNKHTEI | IEEDTNKDKP | NYQFGGHNSV | |
| DFEEDTLPQV | SGHNEGQQTI | EEDTTPPIVP | PTPPTPEVPS | EPETPTPPTP | |
| EVPSEPETPT | PPTPEVPTEP | GKPIPPAKEE | PKKPSKPVEQ | GKVVTPVIEI | |
| NEKVKAVVPT | KKAQSKKSEL | PETGGEESTN | NGMLFGGLFS | ILGLALLRRN | KKNHKA |

The invention further comprises a plasmid or phage comprising a nucleotide sequence coding for said fibronectin binding protein.

The invention further comprises a microorganism containing at least one hybrid-DNA-molecule according to the above. The plasmid pFR001 in an *E. coli* strain 259 has been deposited at the Deutsche Sammlung von Mikroorganismen (DSM), and has thereby been allocated the deposition number DSM 4124.

The invention further comprises a method for producing a fibronectin binding protein whereby at least one hybrid-DNA-molecule of above is transferred into a microorganism, cultivating said microorganism in a growth medium, and isolating the protein thus formed by means of affinity chromatography on a coloumn containing fibronectin bound to an insolubilized carrier followed by ion exchange chromatography.

A further aspect of the invention comprises a chemical synthesis of the fibronectin binding protein, whereby an amino acid sequence is built up based on said nucleotide sequence encoding for said protein starting from the C-terminal alanine which is stepwise reacted with the appropriate amino acid, whereby it is finally reacted with isoleucine at the N-terminal end, to form the fibronectin binding peptide region.

Appropriate carrier proteins can be coupled to the amino acid sequence as well, such as IgG binding regions of protein A.

The invention will be described in the following with reference to the examples given, however, without being restricted thereto.

EXAMPLE

Chemical synthesis of a polypeptide based on the nucleotide sequence coding for the fibronectin binding domain was performed by building up the amino acid sequence corresponding to said nucleotide sequence starting from the C-terminal alanine and stepwise reacting with the appropriate amino acid and finally reacting with the isoleucine at the N-terminal end, in a solid phase synthesis according to the method by K. B. Merrifield, J. Am. Chem. Soc. 86, pp.304, (1964).

MATERIALS AND METHODS

Microorganism growth medium. For growth of *E. coli* bacteria the following medium was used. The amounts given relates to 1 litre of medium.

| | |
|---|---|
| Trypton Soy Broth (Oxoid Ltd. Basingstoke. Hants. GB) | 30 g |
| Yeast Extract (Oxoid) | 10 g |
| D-glucose | 40 g |
| NH$_4$Cl | 2.5 g |
| Na$_2$HPO$_4$.2H$_2$O | 7.5 g |
| KH$_2$PO$_4$ | 3.0 g |
| Na$_2$SO$_4$.10H$_2$O | 2.5 g |
| MgSO$_4$.7H$_2$O | 0.2 g |
| CaCl$_2$.2H$_2$O | 0.5 mg |
| FeCl$_3$.6H$_2$O | 16.7 mg |
| ZnSO$_4$.7H$_2$O | 0.18 mg |
| CuSO$_4$.5H$_2$O | 0.16 mg |
| MnSO$_4$.4H$_2$O | 0.15 mg |
| CoCl$_2$ | 0.10 mg |
| NaEDTA | 20.1 mg |

Assay of Fibronectin Binding Protein (FNBP)

Lysates of *E. coli* clones prepared in Tris-HCl buffer, containing lysozyme EDTA as earlier described (13), were analysed for fibronectin binding activity by measuring their ability to compete with staphylococcal cells for binding the $^{125}$I-labelled 29 kD NH$_2$-terminal fragment of fibronectin. The amount of FNBP able to inhibit binding to 50% is considered as one unit of activity. Bovine fibronectin was provided by Dr. S. Johansson the Department of Medical and Physiological Chemistry, University of Uppsala, Sweden. Overnight cultures of *E. coli* were concentrated 10 times followed by lysis in 0.01M Tris-HCl, 0.001 EDTA, pH 7.9, 1 mg/ml of lysozyme. 100 μl lysate was mixed with 100

μl staphylococcal cells, 100 μl $^{125}$I bovinefibronectin (20000 cpm/ml), 200 μl PBS, and the mixture was incubated for 2 hrs at 20° C. After washing twice in PBS containing 0.1% BSA and 0.05% Tween the radioactivity of the mixture was measured in a gamma counter.

Iodinnation $^{125}$I-labelling of fibronectin and fibronectin fragments was performed using the chloramine-T method.

Bacterial Strains and Plasmids

E. coli TG-1 and DH-5alfa were used as bacterial hosts. The plasmid vectors were pBR322 and pUC18. Table 1 lists the plasmids.

Media and Growth Conditions

E. coli clones were grown in Luria Broth (LB) supplemented with ampicillin at 50 /μg/ml and shaken at 37° C. The optical density was measured with a Linson 3,1 Photometer read at 540 nm. S. aureus was grown in Trypticase Soya Broth (TSB).

Restriction endonucleases and other enzymes. Restriction enzymes, T4 DNA ligase and Bal31 were purchased from Promega (Madison, Wis.), International Biotechnologies Inc. (New Haven, Conn.) and Boehringer Mannheim Biochemicals Scandinavia AB. Restriction mapping and fragment isolation were performed with LiCl$_4$ extracted plasmid DNA. Cloning in pUC18 was performed as described by Maniatis et al. Generation of subclones for sequencing was performed by ExoIII digestion using Erase-a-Base System purchased from Promega. E. coli clones were verified by restriction analysis, sequence analysis, and blot hybridazation. DNA sequencing was done by the dideoxynucleotide methods of Sanger et al, with the sequenase DNA sequencing kit purchased from United States Biochemical Corporation Cleveland Ohio, and the K/RT universal sequencing system purchased from Promega. The sequencing samples were analysed by wedge shaped gels using 6% polyacrylamide. Computer programms were used to record and analyse the sequence data.

The isolation of an E. coli clone containing gene 1 and part of gene 2 for a FNBP from S. aureus strain 8325-4 was described earlier. The plasmid pFR050 was constructed from S. aureus by cleaving 8325-4 chromosomal DNA with HindIII and XbaI. Fragments, 3-4 kbp in size were isolated after agarose-gel electroforeses and ligated into pUC18. One clone containing fnbB sequences was isolated by colony hybridization using a synthetic oligonucleotide located downstream the HindIII-site in fnbB as a probe. The oligonucleotide was synthetized with Applied Biosystem 380A oligonucleotide synthetizer using the phosphoamidite method. Computer programms were used to record and analyse the sequence data.

Western Blotting

Separated components were electroblotted onto NC-sheets (nitrocellulose sheets) (Schleicher and Schnell) for 2 hrs, 200V using the miniblot system (LKB) and the buffer system described by Towbin. Subsequently NC-sheets were saturated with 1% BSA in TBS, pH 7.4, for 30 min, and incubated with 2.4 μg/ml bovine fibronectin in TBS, pH 7.4, for 2 hrs. After washing three times using PBS-Tween (0.1%), the NC-sheets were incubated with rabbit anti bovine fibronectin serum diluted 1:1000, which serum was a gift from Biochemical Centre, University of Uppsala, for 1.5 hrs, followed by washing and final incubation with a protein A peroxidase conjugate (prepared from S aureus A676 protein by conjugation with horse radish peroxidase (Boehringer) in a molar ratio of 1:2) for 1.5 hrs. After final washings 3 times with PBS-Tween, 1x with PBS, the blot was developed with 4-chloro-1-naphtol (Sigma).

Cloning of a Gene Coding for a Second Fibronectin Binding Protein

In our previous work it was described the cloning, expression and determination of the sequence of a gene coding for a fibronectin binding protein (gene 1). In a further analysis of these older sequence data it was found a region, located downstream of gene 1, which showed high homology with the beginning of gene 1. In order to determine if this region downstream of gene 1 exhibits a fibronectin binding activity, a 2.8 kb PstI fragment from pFR001 containing a sequence starting 680 bp downstream the stopcodon of gene 1 was introduced into the multilinker of pUC18. Knowing the transcription direction of gene 2 and its reading frame (from left to right in FIG. 1) it was possible to fuse the fragment in the correct reading frame to the lac-Z promoter of pUC18. This plasmid called pFR035, expressed fibronectin binding activity (Table 1 below). Thus there exist two different genes encoding FnBPs. However, when sequencing pFR035 it could not be found any stop codon in the inserted S. aureus DNA, and by comparing fnbA (gene 1) it was obvious that the complete fnbB was not present. By making southern blots of chromosomal DNA cleaved with HindIII alone, and together with other enzymes, we found that digestion with HindIII together with XbaI would generate a 3.5 kbp fragment (including 65 bp already present in pFR035), which most likely also would contain the missing 3'-part of fnbB. The fragment was cloned as described above and was called pFR050.Subclones of the plasmid were derived by digestion of pFR035 with ExoIII from the 3' end for different time periods with subsequent religation of the DNA, as described in Materials and Methods, above.

TABLE 1

Origin and expression of fibronectin binding activity for clones discussed in this invention. Assay for fibronectin binding is described in Materials and Methods, above.

| Clone | Derivation | Fn-binding |
|---|---|---|
| pFR001 | Original isolate | + |
| pFR035 | 2.8 kb PstI fragment from pFR001 | + |
| pFR036 | 2.3 kb HpaI/EcoRI fragment from pFR001 | + |
| pFR035e31 | pFR035 with 1.3 kb deleted from the 3' PstI site (of which 1.1 kb is vector DNA) | − |
| pFR035e35 | as pFR035e31 but 1.47 kb deleted | − |
| pFR050 | Original isolate | + |
| pFR060 | 2.0 kbp NheI/SphI fragment from pFR050 inserted into pFR035 opened with NheI/SphI | + |

Sequence Analysis

A nucleotide sequence of 1928 bp containing a domain encoding a fibronectin binding protein was determined by sequencing the overlapping subclones derived from pFR035 and pFR001 (FIG. 2). One open reading frame encodes a polypeptide of 940 amino acids, starting with a GTG codon at nucleotide 520, and terminating at the end of the clone at nucleotide 3342 (FIG. 2). FnbB, as fnbA (gene 1) has two possible initiation signals for transcription and a potential ribosome binding site (marked in FIG. 2). The start codon is followed by a possible signal sequence which shows 95% homology to that encoded by fnbA (FIG. 2, and 4). By comparison to FnBPA the cleavage site of the signal sequence is located between the second and third in row of three alanine residues. This corresponds to the cleavage site for the native protein isolated from S. aureus strain Newman. Downstream the signal sequence there is a stretch of about 66 amino acids with a 75% homology to the same stretch in fnbA. The following 444 amino acids have only 40% homology towards FnBPA and have several deletions/insertions, so the B-repeats found in FnBPA is not seen in FnBPB (FIG. 2 and 4). However the rest of the peptide (394 aa) is nearly identical to FnBPA, the main difference being the deletion of 14 amino acids in FnBPB. This highly homologous region contains the same repeat (D1-D4 and Wr1-5) found in FnBPA with the exception that Wr1 is lacking. The Wc region and the hydrophobic region M domain as well as the mainly basic C-terminal end is conserved in FnBPB.

Expression of Fibronectin Binding Protein and Identification of the Binding Activity The E. coli clones pFR035 and pFR036 and subclones derived by deleting the gene 2 fragment of pFR035 were lysed and tested for fibronectin binding protein activity in the inhibition assay. Lysate of both clones inhibit $^{125}$I-labelled fibronectin to bind to S. aureus, whereas the subclone pFR035e31, deleted from the 3' terminal of the gene 2 fragment, has lost the activity (FIG. 3). The fibronectin binding protein activity is thus located to the amino acids downstream amino acid no. 535 (FIG. 1). None of these clones include the D-repeates which has been shown to be the only Fn-binding domain in FnBPA. This will imply that FnBPB contains two different Fn-binding domains one region upstream of amino acid 600 and the D-region. Assay of the FnBp. E. coli clones containing different parts of the fnbB were analysed for Fn-binding activity by measuring their ability to compete with staphylococcal cells for binding of $^{125}$I-labelled intact bovine Fn or the 29 kDa N-terminal fragment. Over night cultures of E. coli were concentrated 10 times and lysed in 10 mM Tris-HCl, 1 mM EDTA, pH 7.9, 1 mg/ml lysozyme. 100 /µl supernatant of centrifuged lysate was mixed with 100 /µl staphylococcal cells ($5 \times 10^8$), 100 µl $^{125}$I-bovine Fn (20,000 cpm, 190 MBq/mg), 200 µl PBS and incubated 2 hrs at 20° C. After washing the mixture twice in PBS containing 0.1% BSA and 0.05 Tween$^R$ 20, the radioactivity bound to the bacterial cells was measured in a gamma counter.

Iodination, $^{125}$I-labelling of Fn and Fn fragments were done according to the chloramine-T method.

Molecular Weight Determination

Western blotting of lysate from pFR035 shows a band corresponding to a molecular weight of 100 kDa and several bands of lower molecular weight, which most likely are degradation products of the 100 kDa product since a shift to lower molecular weights is seen upon storage of the material. The difference seen in the processing is probably due to the fact that in pFR035 the FnBPB is fused to the beta-Gal protein, but in pFR036 it utilizes its own initiation signals, so the proteins are slightly different.

The data presented demonstrate that S. aureus has two different genes encoding for FnBPs. The start codon of fnbB is situated 682 bp downstream the stop codon of fnbA. This sequence between fnbA and fnbB contains a possible transcription termination signal located just a few bp downstream the said stop codon. as well as transcription initiation signals located within the 90 bps which preceeds the start codon in fnbB. This implies that the genes are translated from different messenger RNAs. The region between these transcriptional signals does not contain any open reading frames preceeded by a ribosomal binding site on either strand. The 350 bp region upstream the promotor sequence of fnbB show strong homology with the analogous region of fnbA. In fnbA the binding activity has been localised to the D-repeate domain (between aa 745 and 872) near the cell wall associated part of the molecule, and a subclone where amino acids 746–1018 was excluded was Fn-binding negative. When the two genes are compared it is evident that there is no repeat region present in the pFR035 and pFR036. Still both express Fn-binding activity, which indicates that a non-homologous nucleotide sequence is present encoding for Fn-binding activity.

The expression of the fibronectin binding protein from gene 2 in E. coli, was lower than expression of gene 1.

The present fibronectin binding protein can be used for immunization, whereby the protein, preferably in combination with a fusion protein to create a large antigen to respond to, is injected in dosages causing immunological reaction in the host mammal. Thus the fibronectin binding protein can be used in vaccination of ruminants against mastitis caused by Staphylococcal infections.

Further, the fibronectin binding protein can be used to block an infection in an open skin wound by wound treatment using the fibronectin binding protein in a suspension. Thus the fibronectin binding protein can be used for the treatment of wounds, e.g. for blocking protein receptors, or for immunization (vaccination). In the latter case the host body produces specific antibodies, which can protect against invasion of bacterial strains comprising such a fibronectin binding protein. Hereby the antibodies block the adherence of the bacterial strains to damaged tissue. Examples of colonizing of a tissue damage are:

a) colonizing of wounds in skin and connective tissue, which wounds have been caused by a mechanical trauma, chemical damage, and/or thermical damage;

b) colonizing of wounds on mucous membranes, such as in the mouth cavity, or in the mammary glands, urethra, or vagina;

c) colonizing on connective tissue proteins, which have been exposed by a minimal tissue damage (microlesion) in connection with epithelium and endothelium (mastitis, heart valve infection, hip exchange surgery).

When using the present FNBP, or the polypeptide, for the purpose of immunization (vaccination) in mammals, including man, the protein, or polypeptide is dispersed in sterile, isotonic saline solution, optionally while adding a pharmaceutically acceptable dispersing agent. Different types of adjuvants can further be used in order to sustain the release in the tissue, and thus expose the protein or the peptide for a longer time to the immundefense system of a body.

A suitable dosage to obtain immunization is 0,5 to 5 μg of FNBP, or polypeptide, per kg bodyweight and injection of immunization. In order to obtain a durable immunization, vaccination should be carried out at more than one consecutive occasions with an interval of 1 to 3 weeks, preferably at three occasions.

When using the present FNBP, or polypeptide, for topical, local administration the protein is dispersed in an isotonic saline solution to a concentration of 25 to 250 μg per ml. The wounds are then treated with such an amount only to obtain a complete wetting of the wound surface. For an average wound thus only a couple of millilitres of solution are used in this way. After treatment using the protein solution the wounds are suitably washed with isotonic saline or another suitable wound treatment solution.

Further the fibronectin binding protein as well as the minimal fibronectin binding site polypeptide, of the present invention can be used to diagnose bacterial infections caused by Staphylococci strains, whereby a fibronectin binding protein of the present invention is immobilized on a solid carrier, such as small latex or Sepharose[R] beads, whereupon sera containing antibodies are allowed to pass and react with the FNBP thus immobilized. The agglutination is then measured by known methods.

Further, the FNBP, or the polypeptide can be used in an ELISA test (Enzyme Linked Immuno Sorbet Assay; E Engvall, Med. Biol. 55, 193, (1977)). Hereby wells in a polystyrene microtitre plate are coated with the FNBP, and incubated over night at 4° C. The plates are then thoroughly washed using PBS containing 0.05% TWEEN 20, and dried. Serial dilution of the patient serum were made in PBS-Tween, were added to the wells, and incubated at 30° C. for 1.5 hrs. After rinsing antihuman-IgG conjugated with an enzyme, or an antibovine-IgG conjugated with an enzyme, respectively, horseradishperoxidase or an alkaline phosphatase, was added to the wells and incubated at 30° C. for 1,5 hrs, whereupon when the IgG has been bound thereto, and after rinsing, an enzyme substrate is added, a p-nitrophosphate in case of an alkaline phosphatase, or ortophenylene diamine substrate (OPD) in case a peroxidase has been used, respectively. The plates comprising the wells were thus then rinsed using a citrate buffer containing 0.055% OPD, and 0.005% $H_2O_2$, and incubated at 30° C. for 10 min. Enzyme reaction was stopped by adding a 4N solution of $H_2SO_4$ to each well. The colour development was measured using a spectrophotometer.

Depending on the type of enzyme substrate used a fluoroscense measurement can be used as well.

Another method to diagnose Staphylococci infections is by using the DNA gene probe method based on the FNBP sequence or the polypeptide sequence. Thereby the natural or synthetic DNA sequences are attached to a solid carrier, such as a polystyrene plate as mentioned above, by e.g. adding a milk in the case of diagnozing a mastitis, to the surface. The DNA gene probe, optionally labelled enzymatically, or by a radioactive isotope is then added to the solid surface plate comprising the DNA sequence, whereby the DNA gene probe attaches to the sequence where appearing. The enzyme or the radioactive isotope can then readily be determined by known methods.

Above the term fibronectin binding protein includes the polypeptide sequence as well, which polypeptide sequence forms the minimal fibronectin binding site of the complete protein.

REFERENCES

8. Beachey, E. H. and Simpson, W. A. (1982). Infection 10, 107-110.
9. Courtney, H. S., Ofek, I., Simpson, W. A. Hasty, D. L. and Beachey, E. H. (1986). Infect. Immun. 53, 454-459.
11. Espersen, F. and Clemmensen, I. (1982). Infect. Immun. 37, 526-531.
12. Fröman, G., Switalski, L. M., Speziale, P. and Hook, M. (1987). J. Biol. Chem. 262, 2564-2571
1. Hynes, R. O. (1985) Annu. Rev. Cell Biol. 1, 67-90.
2. Hynes, R. O. (1986) Sci. Ann. 254, 42-51.
6. Kuusela, P. (1978) Nature 276, 718-720.
13. Löfdahl, S., Guss B., Uhlén, M., Philipson, L. and Lindberg, M. (1983) Proc. Natl. Acad. Sci. USA 80, 697-701.
3. Ruoslahti, E. and Pierschbacher, M. D. (1986). Cell, 44, 517-518.
10. Rydén, C., Rubin, K., Speziale, P., Höök, M., Lindberg, M. and Wadström, T. (1983), J. Biol. Chem. 258, 3396-3401.
4. Woods, A., Couchman, J. R., Johansson, S., and Höök, M. (1986), EMBO J. 5, 665-670.
5. Yamada, K. M. (1983), Annu. Rev. Biochem. 52, 761-799.

We claim:

1. A hybrid DNA molecule comprising a nucleotide sequence from S. aureus coding for a protein or polypeptide having fibronectin binding activity, said nucleotide sequence comprising:

| | | |
|---|---|---|
| GTTAACAACA | ATCTTAACTT | TTTATTAACT |
| AAAAACCGAA | CAATATAGAA | TTGCATTTAT |
| ATTTTGCATT | TAAGGGAGAA | TATTATAGTG |
| CATAAGAAAA | CACAAATTGG | GAGCGGCCTC |
| TCGTTGTTGG | AATGGGACAA | GAAAAAGAAG |
| AATACTACAG | TAGAGGAAAG | TGGGAGTTCA |
| CGAAACACAA | ACAACTACAA | ATAACGTTAA |
| CATACAGCGC | GACATCAACT | GAGCAACCAT |
| ACAGAAGAAG | CACCGAAAAC | TGTGCAAGCA |
| AGTTGATTTG | CCATCGGAAA | AAGTTGCTGA |
| AAGTTGACAT | AGCTCAACAA | AGTAAAGTCT |
| AAAAGATCAA | CTGACGTTAC | AGCAGTTGCA |
| AACTAAAGCG | ACAGGTACAG | ATGTAACAAA |
| GTAGTGAAAT | TGTAGGACAT | AAACAAGATA |
| AACGCAGAAA | GAGTAACCTT | GAAATATAAA |
| TAAGGCGGGA | GATTATTTTG | ATTTCACATT |
| ATGGTATCTC | AACACTGCGT | AAAGTTCCGG |
| CAAGTTATGG | CGACAGGAGA | AATAATTGGA |
| GTTTAAAGAA | TATGTACAAG | AAAAGAAAGA |
| TAAATCTATT | TATTGATCCT | ACAACAGTGA |
| GTTGAAGTTA | AATTGGGTGA | GACTACGGTT |
| ATATTTAGGT | GGAGTTAGAG | ATAATTGGGG |
| TTGATACTTT | AAATAAAGTA | GATGGGAAAT |
| AAACCTAACA | ACCAGTCGTT | AAGCTCTGTG |
| TAAAGGAAAT | AAACCAGGGG | TTAATAATCC |
| ACATTGGTTC | AGACGATTTA | GCTGAAAGCG |
| GTCAGCAAAT | TTGAAGATGT | GACTGATAAT |
| TATTGGTGGT | TATTCTTTAA | ACTTTAATAA |
| ATGTAATAAA | ATATGAAGGG | TATTATGATT |
| TTTCAAACAC | ACCTTTTTGG | ATATTATAAC |
| AACTTGGAAA | AATGGCGTTG | CATTTTACTC |
| GCAAAGATAA | ACTAAAGGAA | CCTATTATAG |
| CTTGAATTTA | AATCAGAGCC | GCCAGTGGAG |
| AATCGAAGAA | AGTAATGATT | CTAAGCCAAT |
| CTGTTGAAGG | TGCAGAAGGT | CATGCAGAAG |
| GATTCTATTC | ATGTAGACTT | TGAAGAATCG |
| TCATGCTGAT | GTTGTTGAAT | ATGAAGAAGA |

-continued

| | | |
|---|---|---|
| AGGTTACTAC | TGAGTCTAAC | CTAGTTGAAT |
| GGTATTGTAA | CTGGTGCTGT | TAGCGATCAT |
| AGAATATACG | ACTGAAAGTA | ACTTGATTGA |
| AAGAACATGG | TCAAGCGCAA | GGACCAATCG |
| CATCATATTT | CTCATTCTGG | TTTAGGAACT |
| TGGCGTGATT | GAAGAAATCG | AAGAAAATAG |
| AATTAGGTTA | CGAAGGTGGC | CAAAATAGCG |
| GACACAGAAG | AAGATAAACC | GAAATATGAA |
| TATCGATTTC | GATATGTGTAC | CTCAAATTCA |
| AATCATTCGA | AGAAGATACA | GAGAAGACA |
| GGTAATATCA | TTGATATCGA | CTTCGACAGT |
| CAATAAGCAC | ACTGAAATTA | TTGAAGAAGA |
| ATTATCAATT | CGGTGGACAC | AATAGTGTTG |
| CCACAAGTAA | GTGGTCATAA | TGAAGGTCAA |
| AACACCTCCA | ATCGTGCCAC | CAACGCCACC |
| AGCCGGAAAC | ACCAACACCA | CCGACACCAG |
| ACACCAACAC | CGCCAACGCC | AGAGGTACCA |
| ACCACCTGCT | AAAGAAGAAC | CTAAAAAACC |
| GTAAAGTAGT | AACACCTGTT | ATTGAAATCA |
| GTACCAACTA | AAAAAGCACA | ATCTAAGAAA |
| TGGGAGAAGAA | TCAACAAACA | ACGGCATGTT |
| TTTTAGGTTT | AGCGTTATTA | CGCAGAAATA |
| TCAATCCAAA | ATTGACAGGT | TTATTTCATA |
| TTTTTTAAAA | TTAAAACAAA | TTTCCCAAGA |
| CACTATGAAG | GCGTTCTAAT | TAGTGTTAAA |
| TAATACTTAG | GAAAAGGAGC | ACATTAACTT |
| ATCATTCCCG | CTGCTGGTTT | AGGGACTAGA |

| | |
|---|---|
| CGCTTTTTTT | CATTGCTTTT |
| TGAGTTTTTA | AAATAAATGA |
| AAAAGCAATC | TTAGATACGG |
| AGTATTCTTA | GGAACAATGA |
| CTGCAGCATC | GGAACAAAAC |
| GCTACTGAAA | GTAAAGCAAG |
| TACAATAGAT | GAAACACAAT |
| CACAATCAAC | ACAAGTAACA |
| CCAAAAGTAG | AAACTTCGCG |
| TAAGGAAACT | ACAGGAACTC |
| CAGAAATTAA | ACCAAGAATG |
| GAGAAAGAAG | TAGTGGAAGA |
| TAAAGTGGAA | GTAGAAGAAG |
| CGAATGTTGT | AAATCCTCAT |
| TGGAAATTTG | GAGAAGGAAT |
| AAGCGATAAT | GTTGAAACTC |
| AGATAAAAAG | TACAGATGGT |
| GAAAGAAAAG | TTAGATATAC |
| TTTAACTGCT | GAATTATCTT |
| CGCAAAAAGG | TAACCAAAAT |
| AGCAAAATAT | TTAATATTCA |
| AGTAACAGCT | AATGGTCGAA |
| TTAGTCATTT | TGCGTACATG |
| ACAGTAACTG | GTCAAGTAAC |
| AACAGTTAAG | GTATATAAAC |
| TATATGCAAA | GCTTGATGAT |
| ATGAGTTTAG | ATTTTGATAC |

| | |
|---|---|
| TTTAGACCAA | AGTAAAAATT |
| CAAATGCTAG | CAACTTAGAA |
| TATTATTATA | CAAGTAATTT |
| TAATAACGCT | CAAGGCGACG |
| AACATAGTAC | TCCTATCGAA |
| AAGCATGAAT | TGACTGGTAC |
| TGATTTTGAA | TATCATACAG |
| GTACCATTGA | AACTGAAGAA |
| ACACATGAAA | ATTCAAAACA |
| TACAAACCCA | GGTGGTGGTC |
| TTGACGAAGA | TTCTACAAAA |
| ACAACAATTG | AAGATACGAA |
| ACTAGTAGAT | GAACTACCTG |
| AGGAAATTAC | TGAAAACAAT |
| GAAAATGGTC | ACGGTAATTA |
| CCACGTGGAT | ATTAAGAGTG |
| GTAATCAGTC | ATTTGAGGAA |
| CAAGGTGGCA | ATATCGTAGA |
| TGGTCAAAAT | AATGGTAACC |
| AACCTAAGTA | TGAACAAGGT |
| GTGCCACATA | TTCACGGATT |
| TACAAATAAA | GATAAACCAA |
| ACTTTGAAGA | AGATACACTT |
| CAAACGATTG | AAGAAGATAC |
| GACACCAGAA | GTACCAAGCG |
| AAGTACCAAG | CGAGCCGGAA |
| ACTGAACCTG | GTAAACCAAT |
| TTCTAAACCA | GTGGAACAAG |
| ATGAAAAGGT | TAAAGCAGTG |
| TCTGAACTAC | CTGAAACAGG |
| GTTCGGCGGA | TTATTTAGCA |
| AAAAGAATCA | CAAAGCATAA |
| AATTATATGA | AGTAAGCCTG |
| AATAATTACA | TACTCAATGA |
| ATGACGTTGA | TACATAGATT |
| TGAAAAAAAT | AAAAAAGGCA |
| TTTTTACCAG | CAACTAAAGC. |

2. A microorganism transformed by the hybrid DNA molecule of claim 1.

3. A method for producing a fibronectin binding protein or polypeptide, wherein a) at least one hybrid-DNA-molecule according to claim 1 is introduced into a microorganism, b) said microorganism is cultivated in a growth promoting medium, and c) the protein thus formed is isolated by means of an affinity chromotography on a coloumn with fibronectin bound to an insolubilized carrier followed by ion exchange chromatography.

4. A plasmid or phage comprising a nucleotide sequence from *S. aureus* coding for a protein or polypeptide having fibronectin binding activity, said nucleotide sequence comprising:

| | | | | |
|---|---|---|---|---|
| GTTAACAACA | ATCTTAACTT | TTTATTAACT | CGCTTTTTTT | CATTGCTTTT |
| AAAAACCGAA | CAATATAGAA | TTGCATTTAT | TGAGTTTTTA | AAATAAATGA |
| ATTTTGCATT | TAAGGGAGAA | TATTATAGTG | AAAAGCAATC | TTAGATACGG |
| CATAAGAAAA | CACAAATTGG | GAGCGGCCTC | AGTATTCTTA | GGAACAATGA |
| TCGTTGTTGG | AATGGGACAA | GAAAAAGAAG | CTGCAGCATC | GGAACAAAAC |
| AATACTACAG | TAGAGGAAAG | TGGGAGTTCA | GCTACTGAAA | GTAAAGCAAG |
| CGAAACACAA | ACAACTACAA | ATAACGTTAA | TACAATAGAT | CAAACACAAT |
| CATACGCGC | GACATCAACT | GAGCAACCAT | CACAATCAAC | ACAAGTAACA |
| ACAGAAGAAG | CACCGAAAAC | TGTGCAAGCA | CCAAAAGTAG | AAACTTCGCG |
| AGTTGATTTG | CCATCGGAAA | AAGTTGCTGA | TAAGGAAACT | ACAGGAACTC |
| AAGTTGACAT | AGCTCAACAA | AGTAAAGTCT | CAGAAATTAA | ACCAAGAATG |
| AAAAGATCAA | CTGACGTTAC | AGCAGTTGCA | GAGAAAGAAG | TAGTGGAAGA |
| AACTAAAGCG | ACAGGTACAG | ATGTAACAAA | TAAAGTGGAA | GTAGAAGAAG |
| GTAGTGAAAT | TGTAGGACAT | AAACAAGATA | CGAATGTTGT | AAATCCTCAT |
| AACGCAGAAA | GAGTAACCTT | GAAATATAAA | TGGAAATTTG | GAGAAGGAAT |
| TAAGGCGGGA | GATTATTTTG | ATTTCACATT | AAGCGATAAT | GTTGAAACTC |
| ATGGTATCTC | AACACTGCGT | AAAGTTCCGG | AGATAAAAAG | TACAGATGGT |
| CAAGTTATGG | CGACAGGAGA | AATAATTGGA | GAAAGAAAG | TTAGATATAC |
| GTTTAAAGAA | TATGTACAAG | AAAAGAAAGA | TTTAACTGCT | GAATTATCTT |
| TAAATCTATT | TATTGATCCT | ACAACAAAGG | CGCAAAAAGG | TAACCAAAAT |
| GTTAAGTTA | AATTGGGTGA | GACTACGGTT | AGCAAAATAT | TTAATATTCA |
| ATATTTAGGT | GGAGTTAGAG | ATAATTGGGG | AGTAACAGCT | AATGGTCGAA |
| TTGATACTTT | AAATAAAGTA | GATGGGAAAT | TTAGTCATTT | TGCGTACATG |

-continued

| | | | | |
|---|---|---|---|---|
| AAACCTAACA | ACCAGTCGTT | AAGCTCTGTG | ACAGTAACTG | GTCAAGTAAC |
| TAAAGGAAAT | AAACCAGGGG | TTAATAATCC | AACAGTTAAG | GTATATAAAC |
| ACATTGGTTC | AGACGATTTA | GCTGAAAGCG | TATATGCAAA | GCTTGATGAT |
| GTCAGCAAAT | TTGAAGATGT | GACTGATAAT | ATGAGTTTAG | ATTTTGATAC |
| TAATGGTGGT | TATTCTTTAA | ACTTTAATAA | TTTAGACCAA | AGTAAAAATT |
| ATGTAATAAA | ATATGAAGGG | TATTATGATT | CAAATGCTAG | CAACTTAGAA |
| TTTCAAACAC | ACCTTTTTGG | ATATTATAAC | TATTATTATA | CAAGTAATTT |
| AACTTGGAAA | AATGGCGTTG | CATTTTACTC | TAATAACGCT | CAAGGCGAAG |
| GCAAAGATAA | ACTAAAGGAA | CCTATTATAG | AACATAGTAC | TCCTATCGAA |
| CTTGAATTTA | AATCAGAGCC | GCCAGTGGAG | AAGCATGAAT | TGACTGGTAC |
| AATCGAAGAA | AGTAATGATT | CTAAGCCAAT | TGATTTTGAA | TATCATACAG |
| CTGTTGAAGG | TGCAGAAGGT | CATGCAGAAG | GTACCATTGA | AACTGAAGAA |
| GATTCTATTC | ATGTAGACTT | TGAAGAATCG | ACACATGAAA | ATTCAAAACA |
| TCATGCTGAT | GTTGTTGAAT | ATGAAGAAGA | TACAAACCCA | GGTGGTGGTC |
| AGGTTACTAC | TGAGTCTAAC | CTAGTTGAAT | TTGACGAAGA | TTCTACAAAA |
| GGTATTGTAA | CTGGTGCTGT | TAGCGATCAT | ACAACAATTG | AAGATACGAA |
| AGAATATACG | ACTGAAAGTA | ACTTGATTGA | ACTAGTAGAT | GAACTACCTG |
| AAGAACATGG | TCAAGCGCAA | GGACCAATCG | AGGAAATTAC | TGAAAACAAT |
| CATCATATTT | CTCATTCTGG | TTTAGGAACT | GAAAATGGTC | ACGGTAATTA |
| TGGCGTGATT | GAAGAAATCG | AAGAAAATAG | CCACGTGGAT | ATTAAGAGTG |
| AATTAGGTTA | CGAAGGTGGC | CAAAATAGCG | GTAATCAGTC | ATTTGAGGAA |
| GACACAGAAG | AAGATAAACC | GAAATATGAA | CAAGGTGGCA | ATATCGTAGA |
| TATCGATTTC | GATAGTGTAC | CTCAAATTCA | TGGTCAAAAT | AATGGTAACC |
| AATCATTCGA | AGAAGATACA | GAGAAAGACA | AACCTAAGTA | TGAACAAGGT |
| GGTAATATCA | TTGATATCGA | CTTCGACAGT | GTGCCACATA | TTCACGGATT |
| CAATAAGCAC | ACTGAAATTA | TTGAAGAAGA | TACAAATAAA | GATAAACCAA |
| ATTATCAATT | CGGTGGACAC | AATAGTGTTG | ACTTTGAAGA | AGATACACTT |
| CCACAAGTAA | GTGGTCATAA | TGAAGGTCAA | CAAACGATTG | AAGAAGATAC |
| AACACCTCCA | ATCGTGCCAC | CAACGCCACC | GACACCAGAA | GTACCAAGCG |
| AGCCGGAAAC | ACCAACACCA | CCGACACCAG | AAGTACCAAG | CGAGCCGGAA |
| ACACCAACAC | CGCCAACGCC | AGAGGTACCA | ACTGAACCTG | GTAAACCAAT |
| ACCACCTGCT | AAAGAAGAAC | CTAAAAAACC | TTCTAAACCA | GTGGAACAAG |
| GTAAAGTAGT | AACACCTGTT | ATTGAAATCA | ATGAAAAGGT | TAAAGCAGTG |
| GTACCAACTA | AAAAAGCACA | ATCTAAGAAA | TCTGAACTAC | CTGAAACAGG |
| TGGAGAAGAA | TCAACAAACA | ACGGCATGTT | GTTCGGCGGA | TTATTTAGCA |
| TTTTAGGTTT | AGCGTTATTA | CGCAGAAATA | AAAAGAATCA | CAAAGCATAA |
| TCAATCCAAA | ATTGACAGGT | TTATTTCATA | AATTATATGA | AGTAAGCCTG |
| TTTTTTAAAA | TTAAAACAAA | TTTCCCAAGA | AATAATTACA | TACTCAATGA |
| CACTATGAAG | GCGTTCTAAT | TAGTGTTAAA | ATGACGTTGA | TACATAGATT |
| TAATACTTAG | GAAAAGGAGC | ACATTAACTT | TGAAAAAAAT | AAAAAAGGCA |
| ATCATTCCCG | CTGCTGGTTT | AGGGACTAGA | TTTTTACCAG | CAACTAAAGC |
| TATCGATTTC | GATAGTGTAC | CTCAAATTCA | TGGTCAAAAT | AATGGTAACC |
| AATCATTCGA | AGAAGATACA | GAGAAAGACA | AACCTAAGTA | TGAACAAGGT |
| GGTAATATCA | TTGATATCGA | CTTCGACAGT | GTGCCACATA | TTCACGGATT |
| CAATAAGCAC | ACTGAAATTA | TTGAAGAAGA | TACAAATAAA | GATAAACCAA |
| ATTATCAATT | CGGTGGACAC | AATAGTGTTG | ACTTTGAAGA | AGATACACTT |
| CCACAAGTAA | GTGGTCATAA | TGAAGGTCAA | CAAACGATTG | AAGAAGATAC |
| AACACCTCCA | ATCGTGCCAC | CAACGCCACC | GACACCAGAA | GTACCAAGCG |
| AGCCGGAAAC | ACCAACACCA | CCGACACCAG | AAGTACCAAG | CGAGCCGGAA |
| ACACCAACAC | CGCCAACGCC | AGAGGTACCA | ACTGAACCTG | GTAAACCAAT |
| ACCACCTGCT | AAAGAAGAAC | CTAAAAAACC | TTCTAAACCA | GTGGAACAAG |
| GTAAAGTAGT | AACACCTGTT | ATTGAAATCA | ATGAAAAGGT | TAAAGCAGTG |
| GTACCAACTA | AAAAAGCACA | ATCTAAGAAA | TCTGAACTAC | CTGAAACAGG |
| TGGAGAAGAA | TCAACAAACA | ACGGCATGTT | GTTCGGCGGA | TTATTTAGCA |
| TTTTAGGTTT | AGCGTTATTA | CGCAGAAATA | AAAAGAATCA | CAAAGCATAA |
| TCAATCCAAA | ATTGACAGGT | TTATTTCATA | AATTATATGA | AGTAAGCCTG |
| TTTTTTAAAA | TTAAAACAAA | TTTCCCAAGA | AATAATTACA | TACTCAATGA |
| CACTATGAAG | GCGTTCTAAT | TAGTGTTAAA | ATGACGTTGA | TACATAGATT |
| TAATACTTAG | GAAAAGGAGC | ACATTAACTT | TGAAAAAAAT | AAAAAAGGCA |
| ATCATTCCCG | CTGCTGGTTT | AGGGACTAGA | TTTTTACCAG | CAACTAAAGC |

5. A microorganism containing at least a plasmid or phage according to claim 4.

6. An *E. coli* strain expressing a fibronectin binding protein encoded by the nucleotide sequence:

| | | | | |
|---|---|---|---|---|
| GTTAACAACA | ATCTTAACTT | TTTATTAACT | CGCTTTTTTT | CATTGCTTTT |
| AAAAACCGAA | CAATATAGAA | TTGCATTTAT | TGAGTTTTTA | AAATAAATGA |
| ATTTTGCATT | TAAGGGAGAA | TATTATAGTG | AAAAGCAATC | TTAGATACGG |
| CATAAGAAAA | CACAAATTGG | GAGCGGCCTC | AGTATTCTTA | GGAACAATGA |
| TCGTTGTTGG | AATGGGACAA | GAAAAGAAG | CTGCAGCATC | GGAACAAAAC |
| AATACTACAG | TAGAGGAAAG | TGGGAGTTCA | GCTACTGAAA | GTAAAGCAAG |
| CGAAACACAA | ACAACTACAA | ATAACGTTAA | TACAATAGAT | GAAACACAAT |
| CATACAGCGC | GACATCAACT | GAGCAACCAT | CACAATCAAC | ACAAGTAACA |
| ACAGAAGAAG | CACCGAAAAC | TGTGCAAGCA | CCAAAAGTAG | AAACTTCGCG |
| AGTTGATTTG | CCATCGGAAA | AAGTTGCTGA | TAAGGAAACT | ACAGGAACTC |
| AAGTTGACAT | AGCTCAACAA | AGTAAAGTCT | CAGAAATTAA | ACCAAGAATG |
| AAAAGATCAA | CTGACGTTAC | AGCAGTTGCA | GAGAAAGAAG | TAGTGGAAGA |
| AACTAAAGCG | ACAGGTACAG | ATGTAACAAA | TAAAGTGGAA | GTAGAAGAAG |

-continued

| | | | | |
|---|---|---|---|---|
| GTAGTGAAAT | TGTAGGACAT | AAACAAGATA | CGAATGTTGT | AAATCCTCAT |
| AACGCAGAAA | GAGTAACCTT | GAAATATAAA | TGGAAATTTG | GAGAAGGAAT |
| TAAGGCGGGA | GATTATTTTG | ATTTCACATT | AAGCGATAAT | GTTGAAACTC |
| ATGGTATCTC | AACACTGCGT | AAAGTTCCGG | AGATAAAAAG | TACAGATGGT |
| CAAGTTATGG | CGACAGGAGA | AATAATTGGA | GAAAGAAAAG | TTAGATATAC |
| GTTTAAAGAA | TATGTACAAG | AAAAGAAAGA | TTTAACTGCT | GAATTATCTT |
| TAAATCTATT | TATTGATCCT | ACAACAGTGA | CGCAAAAAGG | TAACCAAAAT |
| GTTGAAGTTA | AATTGGGTGA | GACTACGGTT | AGCAAAATAT | TTAATATTCA |
| ATATTTAGGT | GGAGTTAGAG | ATAATTGGGG | AGTAACAGCT | AATGGTCGAA |
| TTGATACTTT | AAATAAAGTA | GATGGGAAAT | TTAGTCATTT | TGCGTACATG |
| AAACCTAACA | ACCAGTCGTT | AAGCTCTGTG | ACAGTAACTG | GTCAAGTAAC |
| TAAAGGAAAT | AAACCAGGGG | TTAATAATCC | AACAGTTAAG | GTATATAAAC |
| ACATTGGTTC | AGACGATTTA | GCTGAAAGCG | TATATGCAAA | GCTTGATGAT |
| GTCAGCAAAT | TTGAAGATGT | GACTGATAAT | ATGAGTTTAG | ATTTTGATAC |
| TAATGGTGGT | TATTCTTTAA | ACTTTAATAA | TTTAGACCAA | AGTAAAAATT |
| ATGTAATAAA | ATATGAAGGG | TATTATGATT | CAAATGCTAG | CAACTTAGAA |
| TTTCAAACAC | ACCTTTTTGG | ATATTATAAC | TATTATTATA | CAAGTAATTT |
| AACTTGGAAA | AATGGCGTTG | CATTTTACTC | TAATAACGCT | CAAGGCGACG |
| GCAAAGATAA | ACTAAAGGAA | CCTATTATAG | AACATAGTAG | TCCTATCGAA |
| CTTGAATTTA | AATCAGAGCC | GCCAGTGGAG | AAGCATGAAT | TGACTGGTAC |
| AATCGAAGAA | AGTAATGATT | CTAAGCCAAT | TGATTTTGAA | TATCATACAG |
| CTGTTGAAGG | TGCAGAAGGT | CATGCAGAAG | GTACCATTGA | AACTGAAGAA |
| GATTCTATTC | ATGTAGACTT | TGAAGAATCG | ACACATGAAA | ATTCAAAACA |
| TCATGCTGAT | GTTGTTGAAT | ATGAAGAAGA | TACAAACCCA | GGTGGTGGTC |
| AGGTTACTAC | TGAGTCTAAC | CTAGTTGAAT | TTGACGAAGA | TTCTACAAAA |
| GGTATTGTAA | CTGGTGCTGT | TAGCGATCAT | ACAACAATTG | AAGATACGAA |
| AGAATATACG | ACTGAAAGTA | ACTTGATTGA | ACTAGTAGAT | GAACTACCTG |
| AAGAACATGG | TCAAGCGCAA | GGACCAATCG | AGGAAATTAC | TGAAAACAAT |
| CATCATATTT | CTCATTCTGG | TTTAGGAACT | GAAAATGGTC | ACGGTAATTA |
| TGGCGTGATT | GAAGAAATCG | AAGAAAATAG | CCACGTGGAT | ATTAAGAGTG |
| AATTAGGTTA | CGAAGGTGGC | CAAAATAGCG | GTAATCAGTC | ATTTGAGGAA |
| GACACAGAAG | AAGATAAACC | GAAATATGAA | CAAGGTGGCA | ATATCGTAGA |
| TATCGATTTC | GATAGTGTAC | CTCAAATTCA | TGGTCAAAAT | AATGGTAACC |
| AATCATTCGA | AGAAGATACA | GAGAAAGACA | AACCTAAGTA | TGAACAAGGT |
| GGTAATATCA | TTGATATCGA | CTTCGACAGT | GTGCCACATA | TTCACGGATT |
| CAATAAGCAC | ACTGAAATTA | TTGAAGAAGA | TACAAATAAA | GATAAACCAA |
| ATTATCAATT | CGGTGGACAC | AATAGTGTTG | ACTTTGAAGA | AGATACACTT |
| CCACAAGTAA | GTGGTCATAA | TGAAGGTCAA | CAAACGATTG | AAGAAGATAC |
| AACACCTCCA | ATCGTGCCAC | CAACGCCACC | GACACCAGAA | GTACCAAGCG |
| AGCCGGAAAC | ACCAACACCA | CCGACACCAG | AAGTACCAAG | CGAGCCGGAA |
| ACACCAACAC | CGCCAACGCC | AGAGGTACCA | ACTGAACCTG | GTAAACCAAT |
| ACCACCTGCT | AAAGAAGAAC | CTAAAAAACC | TTCTAAACCA | GTGGAACAAG |
| GTAAAGTAGT | AACACCTGTT | ATTGAAATCA | ATGAAAAGGT | TAAAGCAGTG |
| GTACCAACTA | AAAAAGCACA | ATCTAAGAAA | TCTGAACTAC | CTGAAACAGG |
| TGGAGAAGAA | TCAACAAACA | ACGGCATGTT | GTTCGGCGGA | TTATTTAGCA |
| TTTTAGGTTT | AGCGTTATTA | CGCAGAAATA | AAAAGAATCA | CAAAGCATAA |
| TCAATCCAAA | ATTGACAGGT | TTATTTCATA | AATTATATGA | AGTAAGCCTG |
| TTTTTTAAAA | TTAAAACAAA | TTTCCCAAGA | AATAATTACA | TACTCAATGA |
| CACTATGAAG | GCGTTCTAAT | TAGTGTTAAA | ATGACGTTGA | TACATAGATT |
| TAATACTTAG | GAAAAGGAGC | ACATTAACTT | TGAAAAAAAT | AAAAAAGGCA |
| ATCATTCCCG | CTGCTGGTTT | AGGGACTAGA | TTTTTACCAG | CAACTAAAGC. |

\* \* \* \* \*

UNITED STATES PATENT AND TRADEMARK OFFICE
CERTIFICATE OF CORRECTION

PATENT NO. : 5,175,096  
DATED : December 29, 1992  
INVENTOR(S) : Höök et al.

Page 1 of 5

It is certified that error appears in the above-indentified patent and that said Letters Patent is hereby corrected as shown below:

In the Claims, from column 12, please delete the nucleotide sequence which runs from line 36 to column 14, line 32, and insert therefor:

```
GTTAACAACA ATCTTAACTT TTTATTAACT CGCTTTTTTT CATTGCTTTT
AAAAACCGAA CAATATAGAA TTGCATTTAT TGAGTTTTTA AAATAAATGA
ATTTTGCATT TAAGGGAGAA TATTATAGTG AAAAGCAATC TTAGATACGG
CATAAGAAAA CACAAATTGG GAGCGGCCTC AGTATTCTTA GGAACAATGA
TCGTTGTTGG AATGGGACAA GAAAAGAAG CTGCAGCATC GGAACAAAAC
AATACTACAG TAGAGGAAAG TGGGAGTTCA GCTACTGAAA GTAAAGCAAG
CGAAACACAA ACAACTACAA ATAACGTTAA TACAATAGAT GAAACACAAT
CATACAGCGC GACATCAACT GAGCAACCAT CACAATCAAC ACAAGTAACA
ACAGAAGAAG CACCGAAAAC TGTGCAAGCA CCAAAAGTAG AAACTTCGCG
AGTTGATTTG CCATCGGAAA AAGTTGCTGA TAAGGAAACT ACAGGAACTC
AAGTTGACAT AGCTCAACAA AGTAAAGTCT CAGAAATTAA ACCAAGAATG
AAAAGATCAA CTGACGTTAC AGCAGTTGCA GAGAAGAAG TAGTGGAAGA
AACTAAAGCG ACAGGTACAG ATGTAACAAA TAAAGTGGAA GTAGAAGAAG
GTAGTGAAAT TGTAGGACAT AAACAAGATA CGAATGTTGT AAATCCTCAT
AACGCAGAAA GAGTAACCTT GAAATATAAA TGGAAATTTG GAGAAGGAAT
```

UNITED STATES PATENT AND TRADEMARK OFFICE
CERTIFICATE OF CORRECTION

PATENT NO. : 5,175,096

DATED : December 29, 1992

INVENTOR(S) : Höök et al.

Page 2 of 5

It is certified that error appears in the above-indentified patent and that said Letters Patent is hereby corrected as shown below:

```
TAAGGCGGGA GATTATTTTG ATTTCACATT AAGCGATAAT GTTGAAACTC
ATGGTATCTC AACACTGCGT AAAGTTCCGG AGATAAAAAG TACAGATGGT
CAAGTTATGG CGACAGGAGA AATAATTGGA GAAAGAAAAG TTAGATATAC
GTTTAAAGAA TATGTACAAG AAAAGAAAGA TTTAACTGCT GAATTATCTT
TAAATCTATT TATTGATCCT ACAACAGTGA CGCAAAAAGG TAACCAAAAT
GTTGAAGTTA AATTGGGTGA GACTACGGTT AGCAAAATAT TTAATATTCA
ATATTTAGGT GGAGTTAGAG ATAATTGGGG AGTAACAGCT AATGGTCGAA
TTGATACTTT AAATAAAGTA GATGGGAAAT TTAGTCATTT TGCGTACATG
AAACCTAACA ACCAGTCGTT AAGCTCTGTG ACAGTAACTG GTCAAGTAAC
TAAAGGAAAT AAACCAGGGG TTAATAATCC AACAGTTAAG GTATATAAAC
ACATTGGTTC AGACGATTTA GCTGAAAGCG TATATGCAAA GCTTGATGAT
```

UNITED STATES PATENT AND TRADEMARK OFFICE
CERTIFICATE OF CORRECTION

PATENT NO. : 5,175,096  
DATED : December 29, 1992  
INVENTOR(S) : Höök et al.

Page 3 of 5

It is certified that error appears in the above-indentified patent and that said Letters Patent is hereby corrected as shown below:

```
GTCAGCAAAT TTGAAGATGT GACTGATAAT ATGAGTTTAG ATTTTGATAC
TAATGGTGGT TATTCTTTAA ACTTTAATAA TTTAGACCAA AGTAAAAATT
ATGTAATAAA ATATGAAGGG TATTATGATT CAAATGCTAG CAACTTAGAA
TTTCAAACAC ACCTTTTTGG ATATTATAAC TATTATTATA CAAGTAATTT
AACTTGGAAA AATGGCGTTG CATTTTACTC TAATAACGCT CAAGGCGACG
GCAAAGATAA ACTAAGGAA CCTATTATAG AACATAGTAC TCCTATCGAA
CTTGAATTTA AATCAGAGCC GCCAGTGGAG AAGCATGAAT TGACTGGTAC
AATCGAAGAA AGTAATGATT CTAAGCCAAT TGATTTTGAA TATCATACAG
CTGTTGAAGG TGCAGAAGGT CATGCAGAAG GTACCATTGA AACTGAAGAA
GATTCTATTC ATGTAGACTT TGAAGAATCG ACACATGAAA ATTCAAAACA
TCATGCTGAT GTTGTTGAAT ATGAAGAAGA TACAAACCCA GGTGGTGGTC
AGGTTACTAC TGAGTCTAAC CTAGTTGAAT TTGACGAAGA TTCTACAAAA
GGTATTGTAA CTGGTGCTGT TAGCGATCAT ACAACAATTG AAGATACGAA
AGAATATACG ACTGAAAGTA ACTTGATTGA ACTAGTAGAT GAACTACCTG
```

UNITED STATES PATENT AND TRADEMARK OFFICE
CERTIFICATE OF CORRECTION

PATENT NO. : 5,175,096  
DATED : December 29, 1992  
INVENTOR(S) : Höök et al.

Page 4 of 5

It is certified that error appears in the above-indentified patent and that said Letters Patent is hereby corrected as shown below:

```
AAGAACATGG  TCAAGCGCAA  GGACCAATCG  AGGAAATTAC  TGAAAACAAT
CATCATATTT  CTCATTCTGG  TTTAGGAACT  GAAAATGGTC  ACGGTAATTA
TGGCGTGATT  GAAGAAATCG  AAGAAAATAG  CCACGTGGAT  ATTAAGAGTG
AATTAGGTTA  CGAAGGTGGC  CAAAATAGCG  GTAATCAGTC  ATTTGAGGAA
GACACAGAAG  AAGATAAACC  GAAATATGAA  CAAGGTGGCA  ATATCGTAGA
TATCGATTTC  GATAGTGTAC  CTCAAATTCA  TGGTCAAAAT  AATGGTAACC
AATCATTCGA  AGAAGATACA  GAGAAGACA   AACCTAAGTA  TGAACAAGGT
GGTAATATCA  TTGATATCGA  CTTCGACAGT  GTGCCACATA  TTCACGGATT
CAATAAGCAC  ACTGAAATTA  TTGAAGAAGA  TACAAATAAA  GATAAACCAA
ATTATCAATT  CGGTGGACAC  AATAGTGTTG  ACTTTGAAGA  AGATACACTT
CCACAAGTAA  GTGGTCATAA  TGAAGGTCAA  CAAACGATTG  AAGAAGATAC
AACACCTCCA  ATCGTGCCAC  CAACGCCACC  GACACCAGAA  GTACCAAGCG
AGCCGGAAAC  ACCAACACCA  CCGACACCAG  AAGTACCAAG  CGAGCCGGAA
ACACCAACAC  CGCCAACGCC  AGAGGTACCA  ACTGAACCTG  GTAAACCAAT
ACCACCTGCT  AAAGAAGAAC  CTAAAAAACC  TTCTAAACCA  GTGGAACAAG
GTAAAGTAGT  AACACCTGTT  ATTGAAATCA  ATGAAAAGGT  TAAAGCAGTG
```

UNITED STATES PATENT AND TRADEMARK OFFICE
CERTIFICATE OF CORRECTION

PATENT NO. : 5,175,096

DATED : December 29, 1992

INVENTOR(S) : Höök et al.

It is certified that error appears in the above-indentified patent and that said Letters Patent is hereby corrected as shown below:

```
GTACCAACTA  AAAAAGCACA  ATCTAAGAAA  TCTGAACTAC  CTGAAACAGG
TGGAGAAGAA  TCAACAAACA  ACGGCATGTT  GTTCGGCGGA  TTATTTAGCA
TTTTAGGTTT  AGCGTTATTA  CGCAGAAATA  AAAAGAATCA  CAAAGCATAA
TCAATCCAAA  ATTGACAGGT  TTATTTCATA  AATTATATGA  AGTAAGCCTG
TTTTTTAAAA  TTAAAACAAA  TTTCCCAAGA  AATAATTACA  TACTCAATGA
CACTATGAAG  GCGTTCTAAT  TAGTGTTAAA  ATGACGTTGA  TACATAGATT
TAATACTTAG  GAAAGGAGC   ACATTAACTT  TGAAAAAAAT  AAAAAGGCA
ATCATTCCCG  CTGCTGGTTT  AGGGACTAGA  TTTTTACCAG  CAACTAAAGC
```

Signed and Sealed this

Twenty-fourth Day of December, 1996

Attest:

BRUCE LEHMAN

*Attesting Officer*   *Commissioner of Patents and Trademarks*

UNITED STATES PATENT AND TRADEMARK OFFICE
CERTIFICATE OF CORRECTION

PATENT NO.   : 5,175,096
DATED        : December 29, 1992
INVENTOR(S)  : Magnus Hook et al.

Page 1 of 1

It is certified that error appears in the above-identified patent and that said Letters Patent is hereby corrected as shown below:

Figure 4,
Please delete amino acid 100 "O" and insert -- Q -- such that amino acids 91-100 read as -- TTEEAPKTVQ --.

Columns 3-4,
In the amino acid sequence bridging columns 3-4, please delete the last set of amino acids in the second row "TTEEAPKTVO" and insert -- TTEEAPKTVQ --.

Columns 5-6,
Between lines 33 and 44, please delete "DFEESTHHEN" in the first row and second column of the amino acid sequence and insert -- DFEESTHEN --; and please delete "DKPKYEQGGG" in the fourth row and second column of the amino acid sequence and insert -- DKPKYEQGG --.

Signed and Sealed this

Twenty-eighth Day of May, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO. : 5,175,096                                          Page 1 of 1
DATED       : December 29, 1992
INVENTOR(S) : Magnus Hook et al.

It is certified that error appears in the above-identified patent and that said Letters Patent is hereby corrected as shown below:

Drawings,
Figure 4, please delete amino acid 100 "O" and insert -- Q -- such that amino acids 91-100 read as -- TTEEAPKTVQ --.

Columns 3-4,
In the amino acid sequence bridging columns 3-4, please delete the last set of amino acids in the second row "TTEEAPKTVO" and insert -- TTEEAPKTVQ --.

Columns 5-6,
Between lines 33 and 44, please delete "DFEESTHHEN" in the first row and second column of the amino acid sequence and insert -- DFEESTHEN --.
Between lines 33 and 44, please delete "DKPKYEQGGG" in the fourth row and second column of the amino acid sequence and insert -- DKPKYEQGG --.

Signed and Sealed this

Twelfth Day of November, 2002

Attest:

Attesting Officer

JAMES E. ROGAN
Director of the United States Patent and Trademark Office